United States Patent [19]

Dean

[11] Patent Number: 5,064,963
[45] Date of Patent: Nov. 12, 1991

[54] PROCESS FOR THE SYNTHESIS OF N-(3-(1H-IMIDAZOL-1-YL)PHENYL-4-(SUBSTITUTED)-2-PYRIMIDINAMINES

[75] Inventor: William D. Dean, Congers, N.Y.

[73] Assignee: American Cyanamid Company, Stamford, Conn.

[21] Appl. No.: 514,455

[22] Filed: Apr. 25, 1990

[51] Int. Cl.$^5$ ............................................ C07D 403/04
[52] U.S. Cl. .................................... 544/331; 544/332
[58] Field of Search ................................ 544/332, 331

[56] References Cited

U.S. PATENT DOCUMENTS 4,788,195  11/1986  Torley ................................. 514/252

OTHER PUBLICATIONS

J. Medicinal Chemistry, 1975, vol. 18, No. 11, pp. 1077–1088.
Synthesis, Sep. 1986, pp. 777–779.

Primary Examiner—Mukund J. Shah
Assistant Examiner—Matthew V. Grumbling
Attorney, Agent, or Firm—Thomas S. Szatkowski

[57] ABSTRACT

The invention provides a novel process for producing N-[3-(1H-imidazol-1-yl)phenyl]-4-(substituted)-2 pyrimidinamine compounds in which the substituent is a 2-pyridinyl, 3-pyrindinyl, 4-pyridinyl, 2-furanyl or 2-thienyl group. The process includes the steps of (1) reacting a 3-(1H-imidazol-1-yl)benzamine with cyanamide and a halogen acid while controlling the pH of the reaction between pH about 2 to abourt 3.5 and recovering a [3-(1H-imidazol-1-yl)phenyl] guanidine dihydrohalide and (2) reacting the [3-(1H-imidazol-1-yl)phenyl] guanidine dihydrohalide so recovered with an appropriately substituted 3-dimethylamino-1-(substituted)-2-propen-1-one and a base at a pH of from about 10.5 to about 11.5 and recovering the N-[3-(1H-imidazol-1-yl)phenyl-4-(substituted)-2-pyrimidamine compound so produced. The novel process provides improved yield and purity by adhering to the stated crucial pH ranges.

5 Claims, No Drawings

PROCESS FOR THE SYNTHESIS OF N-(3-(1H-IMIDAZOL-1-YL)PHENYL-4-(SUBSTITUTED)-2-PYRIMIDINAMINES

BACKGROUND OF THE INVENTION

1. Field of the Invention

The invention is concerned with an improved process for the large scale production of N-[3-(1H-imidazol-1-yl)phenyl]-4-(substituted)-2-pyrimidinamines, wherein the substituent is selected from the group consisting of 2-pyridinyl, 3-pyridinyl, 4-pyridinyl, 2-furanyl and 2-thienyl.

2. Description of the Prior Art

As disclosed in U.S. Pat. No. 4,788,195, the N-[3-(1H-imidazol-1-yl)phenyl]-4-(substituted)-2-pyrimidinamine compounds are known anti-asthma agents. This patent also discloses a method for producing such compounds from [3-(1H-imidazol-1-yl)phenyl]guanidine and an appropriate enaminone.

The '195 patent describes making the guanidine by adding 3-(1H-imidazol-1-yl)benzamine to a solution of HCL, in ethanol, adding cyanamide and warming. This method of making a guanidine from the reaction of the mineral acid salt of an amine with cyanamide is well known (See J. Medicinal Chemistry, 1975, vol 18 no. 11 p 1077–10883 and Synthesis, September 1986, p 777–779). These references do not disclose or suggest controlling pH within any particular range during the amine, HCL and cyanamide reaction to form the guanidine.

The '195 patent describes forming the desired N-[3-(1H-imidazol-1-yl)phenyl]-4-(substituted)-2-pyrimidinamines by reacting the crude guanidine without further purification with an appropriate enaminone in the presence of a base. The desired products are recovered by precipitation and recrystallization steps. Example 328 of U.S. Pat. No. 4,788,195 describes the formation of N-[3-(1H-imidazol-1-yl)phenyl]-4-(2-pyridinyl)-2pyrimidinaine at a yield of 26%. Other relevant Examples include 220, 231, 232 and 233. While these described procedures and yields are quite acceptable on an experimental scale, a greater yield would be more desirable for a large scale or commercial process.

SUMMARY OF THE INVENTION

It has now been found that improved yields of N-[3-(1H-imidazol-1-yl)phenyl]-4-(2-substituted)-2-pyrimidinamines are obtained by:

a) controlling the pH between about 2 to about 3.5 with HCL gas during the reaction of 3-(1H-imidazol-1-yl)benzamine with cyanamide to form [3-1H-imidazol-1-yl)phenyl]guanidine; and b) reacting the [3-1H-imidazol-1-yl)phenyl]guanidine so formed with an appropriate enaminone at a pH of about 10.5 to about 11.5.

In the formation of the [3-(1H-imidazol-1-yl) phenyl]-guanidine, it has unexpectedly been found that a product of extremely high purity and in high yield is obtained by maintaining the pH at a level of between about 2 to about 3.5 throughout the reaction. In contrast, the known prior art methods employ a fixed amount of HCL which would be depleted as the reaction proceeded and result in an increasing of the pH. Such an increased pH contributes to poorer yields and purity due to an incomplete reaction.

In the formation of the N-[3-(1H-imidazol-1-yl)phenyl]-4-(substituted)-2-pyrimidinamines by reaction of the guanidine with an enaminone, it has unexpectedly been found that at an optimum pH range of about 10.5 to about 11.5 the product is obtained at significantly higher yield and purity than heretofore.

The improvements according to the present invention resulted in a three times increase in yield without the need for fractional crystallization, a decrease in the reaction time from 3 days to 2 days, and a production of a pure product which eliminated the need for further purification.

DETAILED DESCRIPTION OF INVENTION

The following Scheme I illustrates the improved process of the present invention. In Scheme I, 3-(1H-imidazol-1-yl)benzamine (1) is reacted with cyanamide to produce [3-(1H-imidazol-1-yl)phenyl]guanidine dihydrochloride (2) which is reacted with the enaminone (3), 3-dimethylamino-1-(2-pyridinyl)-2-propene-1-one, to produce the product (4), N-[3-(1H-imidazol-1-yl)phenyl]-4-(2-pyridinyl)-2-pyrimidinamine.

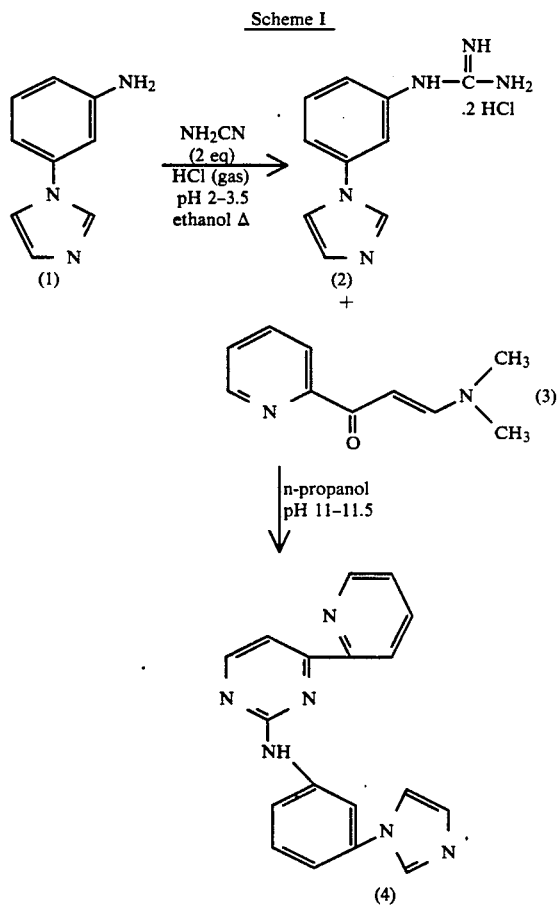

In accordance with Scheme I, the conversion of 3-(1H-imidazol-1-yl)benzamine (1) to [3-(1H-imidazol-1-yl)phenyl]guanidine, dihydrochloride (2) is carried out with 2 equivalents of solid cyanamide in ethanol followed by addition of dry gaseous hydrogen chloride to pH 2 and refluxed gently on a steam bath for 5 hours. The pH is controlled between about pH 2.0 to about pH 3.5 during the refluxing by intermittently measuring the pH and carefully adding a sufficent amount of dry gaseous hydrogen chloride to maintain the pH within the stated range. Of course, other methods of controlling the pH will be readily apparent to those skilled in the art and are contemplated to be useful to the method of the invention. This improvement results in the isolation of pure crystalline [3-(1H-imidazol-1-yl)phenyl]guanidine, dihydrochloride (2) in 75-90% yields.

The reaction of 3-(1H-imidazol-1-yl)benzamine (1), using the conditions described in Example 328 U.S. Pat. No. 4,788,195, and cyanamide resulted only in the formation of mixtures of unreacted (1) and the desired guanidine monohydrochloride as a brown oil.

When using the procedure in U.S. Pat. No. 4,788,195, the reaction of [3-1H-imidazol-1-yl) phenyl]guanidine, monohydrochloride with 3-dimethylamino-1-(2-pyridyl)-2-propen-1-one, potassium carbonate, as the base, and methoxyethanol, as the solvent, resulted in the formation of black by-products. It has now been found that 3-dimethylamino-1-(2-pyridyl)-2-propen-1-one is stable in basic or neutral media but decomposes rapidly on exposure to acids. It has further been found that at a pH of about 10.5 to about 11.5 preferably about 11 to about 11.5 the desired products are formed in good yield and purity. Outside of this pH range, the yield is substantially worse.

The [3-1H-Imidazol-1-yl)phenyl]guanidine, dihydrochloride (2) is then treated in refluxing n-propanol with 2 equivalents of 10N sodium hydroxide (pH 11) followed by an equivalent amount of 3-dimethylamino-1-(2-pyridyl)-2-propen-1-one(3). After 18 hours of refluxing the reaction is complete and the desired product, N-[3-(1H-imidazol-1-yl)phenyl]-4-(2-pyridinyl)2-pyrimidinamine (4) is isolated free of decomposition products. The purification of the crude material is accomplished by slurring the product in water to remove any inorganics. Use of the above improvements allows preparation of N-[3(1H-imidazol-1-yl)phenyl]-4-(2-pyridinyl)-2-pyrimidinamine (4) in 65-75% overall yield based on 3-(1H-imidazol-1-yl) benzamine (1) as compared with 25-30% overall yield obtained using the procedure in Example 328 of U.S. Pat. No. 4,788,195.

Enaminones (3) other then 3-dimethylamino-1-(2-pyridyl)-2-propen-1-one may be employed with similar result. For examples, the following enaiminones may be employed in the process according to the present invention:

3-dimethylamino-1-(3-pyridyl)-2-propen-1-one,
3-dimethylamino-1-(4-pyridyl)-2-propen-1-one,
3-dimethylamino-1-(2-furyl)-2-propen-1-one,
3-dimethylamino-1-(2-thienyl)-2-propen-1-one.

EXAMPLE 1

[3-(1H-Imidazol-1-yl)phenyl]guanidine, dihydrochloride (2)

One hundred and sixty g of 3 (1H-imidazol-1-yl)benzenamine (1) is dissolved in 1 liter of hot absolute ethanol. Dry hydrogen chloride gas is bubbled into the hot solution to pH 3, 42 g of solid cyanamide is added and the solution heated for 5 minutes (pH 4). The pH is brought back to pH 3 with dry hydrogen chloride gas, 42 g of solid cyanamide is added, the reaction is heated on a steam bath for 5 hours, an additional 6 g of solid cyanamide is added and the reaction continued for 1.5 hours. The pH is monitored throughout the reaction and maintained between pH 2.5 and 3.0 by the addition of dry hydrogen chloride gas. The hot reaction mixture is filtered and the collected solid washed with three 200 ml portions of hot ethanol followed by 500 ml of diethyl ether. The crystalline solid is air dried overnight giving 205 g (86% yield) of desired product as the dihydrochloride, mp 252°-254° C.

EXAMPLE 2

N-[3-(1H-Imidazol-1-yl)phenyl]-4-(2-pyridinyl)-2-pyrimidinamine (4)

Thirteen and seven tenths grams of [3-(1H-imidazol-1-yl)phenyl]guanidine, dihydrochloride (2) from Example 1, 8.8 g of 3-dimethylamino-1-(2-pyridyl)-2-propen-1-one (3), 50 ml of n-propanol and 10 ml of 10N sodium hydroxide is refluxed for 18 hours. The reaction is diluted with 50 ml of n-propanol and filtered. The collected yellow solid is stirred in 300 ml of water for 0.5 hour, filtered and washed with 50 ml of n-propanol followed by 100 ml of diethyl ether. The solid is air dried overnight giving 13.4 g (85%) of the desired product, mp 210°-211° C. The overall yield following this procedure is 73%.

EXAMPLES 3-6

Effect of pH On the Reaction Of [3-(1H imidazol-1-yl)phenyl guanidine dihydrochloride (2) With 3-dimethylamino-1-(2 pyridyl)-2-propen-1-one (3)

The reaction of 0.01 mole of [3-(1H-imidazol-1- yl)-phenyl guanidine (2) with 0.01 mole of 3-dimethylamino-1-(2pyridyl)-2-propen-1-one enaminone (3) is examined to determine the effect of the reaction pH on yield and purity of the product, N-[3-(1H-imidazol-1-yl)phenyl]-4-(2-pyridenyl)-2-pyrimidinamine (4). Two bases are utilized, solid potassium carbonate and 10N aqueous sodium hydroxide. All reactions are run in refluxing n-propanol for approximately twenty-four (24) hours. The products are isolated by quenching the reaction mixture including any precipitated solids into water followed by filtration. These filtered solids are re-suspended in water to remove inorganic salts, filtered and air dried to give the final products. The results of these experiments are shown in Table I. In the case of reactions at pH=11 (Examples 3 and 5), a clean product is isolated using either potassium carbonate or 10N sodium hydroxide. Referring to Table I, 10N sodium hydroxide worked better than potassium carbonate as can be observed from the yields and melting points of the products. At pH=9 (Example 4, NaOH) a low yield of a dark gray solid is obtained and at pH=12 (Example 6) only water soluble products are formed. No products resembling N-[3-(1H-imidazol-1-yl)phenyl]-4-(2-pyridinyl)-2-pyrimidinamine could be isolated at pH=12. These experiments clearly indicate that regardless of the base used, there is an optimum pH range of about 10.5 to about 11.5 for this reaction.

TABLE I

| EXAMPLE | BASE | MOLES OF BASE | pH | PRODUCT WEIGHT | YIELDS | MP° C. |
| --- | --- | --- | --- | --- | --- | --- |
| 3 | K$_2$CO$_3$ | 0.05 | 11 | 1.9 g | 60.5%* | 208-210° C. |
| 4 | 10N NaOH | 0.01 | 9 | 0.60 g | 19%** | 205-207° C. |
| 5 | 10N NaOH | 0.02 | 11 | 2.05 g | 65%* | 209.5-210° C. |

TABLE I-continued

| EXAMPLE | BASE | MOLES OF BASE | pH | PRODUCT WEIGHT | YIELDS | MP° C. |
|---|---|---|---|---|---|---|
| 6. | 10N NaOH | 0.03 | 12 | 0 | 0 | — |

*yellow crystalline material
**dark grey solid

EXAMPLE 7

N-[3-(1H-imidazol-1-yl)phenyl]-4-(3-pyridinyl)-2-pyrimidinamine

Two and 73 hundredths grams of [3-(1H-imidazol-1-yl)phenyl]guanidine, dihydrochloride (2) from Example 1, 1.76 grams of 3-dimethylamino-1-(3-pyridyl)-2-propen-1-one, 25 ml of n-propanol and 2 equivalents (2 ml) of 10N NaOH at pH=11 is refluxed for twenty-four (24) hours. The products are isolated by quenching the reaction mixture including any precipitated solids into water followed by filtration. These filtered solids are re-suspended in water to remove inorganic salts, filtered and air dried to give 2.1 g (67% yield) of the desired product, mp 95°-120° C.

EXAMPLE 8

N-[3-(1H-imdazol-1-yl)phenyl]-4-(4-pyridinyl)-2-pyrimidinamine

Two and 73 hundredths grams of [3-(1H-imidazol-1-yl)phenyl]guanidine, dihydrochloride (2) from Example 1, 1.76 grams of 3-dimethylamino-1-(4-pyridyl)-2-propen-1-one, 25 ml of n-propanol and 2 equivalents (2 ml) of 10N NaOH at pH=11 is refluxed for twenty-four (24) hours. The products are isolated by quenching the reaction mixture including any precipitated solids into water followed by filtration. These filtered solids are re-suspended in water to remove inorganic salts, filtered and air dried to give 2.2 g (70% yield) of the desired product, mp 244°-245° C.

EXAMPLE 9

4-(2-furanyl)-N-[3-(1H-imidazol-1-yl)phenyl]-2-pyrimidinamine

Two and 73 hundredths grams of [3-(1H-imidazol-1-yl)phenyl]guanidine, dihydrochloride (2) from Example 1, 1.6 grams of 3-dimethylamino-1-(2-furyl)-2-methyl-2-propen-1-one, 25 ml of n-propanol and 2 equivalents (2 ml) of 10N NaOH at pH=11 is refluxed for twenty-four (24) hours. The products are isolated by quenching the reaction mixture including any precipitated solids into water followed by filtration. These filtered solids are re-suspended in water to remove inorganic salts, filtered and air dried to give 1.35 g (44.5% yield) of the desired product, mp 175°-178° C.

EXAMPLE 10

N-[3-(1H-imidazo-1-lyl)phenyl]-4(2-thienyl)-2-pyrimdinamine

Two and 73 hundredths grams of [3-(1H-imidazol-1-yl)phenyl]guanidine, dihydrochloride (2) from Example 1, 1.81 grams of 3-dimethylamino-1-(2-thienyl)-2-propen-1-one, 25 ml n-propanol and 2 equivalents (2 ml) of 10N NaOH at pH=11 is refluxed for twenty-four (24) hours. The products are isolated by quenching the reaction mixture including any precipitated solids into water followed by filtration. These filtered solids are re-suspended in water to remove inorganic salts, filtered and air dried to give 1.0 g (31.3% yield) of the desired product, mp 192°-194° C.

I claim:

1. A process for producing N-[3-(1H-imidazol-1-yl)phenyl]-4-(substituted)-2-pyrimidinamine wherein substituents are selected from the group consisting of 2-pyridinyl, 3-pyridinyl, 4-pyridinyl, 2-furanyl amd 2-thienyl which comprises:
   (A) reacting 3-(1H-imidazol-1-yl) benzamine with cyanamide and a halogen acid, while controlling the pH of the reaction between pH about 2 to about 3.5 and recovering [3-(1H-imidazol-1-yl)phenyl]-guanidine, dihydrohalide; and
   (B) reacting the [3-(1H-imidazol-1-yl)phenyl]guanidine, dihydrohalide so recovered with a 3-dimethylamino-1-(substituted)-2-propen-1-one and a base in an appropriate solvent at a pH of from about 10.5 to about 11.5 and recovering N-[3-1H-imidazol-1-yl)phenyl]-4-(substituted)-2-pyrimidinamine.

2. The process of claim 1 wherein said halogen acid comprises hydrogen bromide, or hydrogen chloride.

3. The process of claim 2 wherein said halogen acid comprises gaseous hydrogen chloride.

4. The process of claim 1 wherein said base comprises 10N NaOH.

5. The process of claim 1 wherein said [3-(1H-imidazol-1-yl)phenyl]guanidine, dihydrohalide is recovered by filtration.

* * * * *